(12) United States Patent
Giordano

(10) Patent No.: US 8,940,402 B2
(45) Date of Patent: Jan. 27, 2015

(54) MULTICOLOR DENTAL BLANKS AND RELATED METHODS

(76) Inventor: Russell A. Giordano, Marlborough, MA (US)

( * ) Notice: Subject to any disclaimer, the term of this patent is extended or adjusted under 35 U.S.C. 154(b) by 1089 days.

(21) Appl. No.: 12/934,618

(22) PCT Filed: Dec. 28, 2007

(86) PCT No.: PCT/US2007/089157
§ 371 (c)(1),
(2), (4) Date: Jan. 18, 2011

(87) PCT Pub. No.: WO2008/083358
PCT Pub. Date: Jul. 10, 2008

(65) Prior Publication Data
US 2011/0104643 A1   May 5, 2011

Related U.S. Application Data (60) Provisional application No. 60/878,041, filed on Dec. 28, 2006.

(51) Int. Cl.
*A61C 13/09*      (2006.01)
*A61C 13/34*      (2006.01)
*A61C 13/00*      (2006.01)

(52) U.S. Cl.
CPC .............. *A61C 13/34* (2013.01); *A61C 13/0022* (2013.01); *A61C 13/00* (2013.01)
USPC .................... 428/542.8; 433/202.1; 433/203.1

(58) Field of Classification Search
CPC .. A61C 13/0022; A61C 13/09; A61C 13/206; A61C 13/0019; A61C 13/08; A61C 13/082; C04B 2235/9653; C04B 2235/9661; B32B 2535/00; B32B 2250/03; B32B 2250/04
USPC ................. 428/542.8; 433/202.1, 203.1, 229; 264/16, 20
See application file for complete search history.

(56) References Cited

U.S. PATENT DOCUMENTS 3,802,783 A    4/1974  Simmonds et al.
4,650,418 A  *  3/1987  Blair et al. ................. 433/203.1
(Continued)

FOREIGN PATENT DOCUMENTS

| DE | 19654055 A1 * | 6/1998 | ............. A61C 13/34 |
| EP | 125867 A1 | 10/2002 | |
| SU | 1683733 A1 * | 10/1991 | ............. A61C 13/09 |

OTHER PUBLICATIONS

Vita Zahnfabrik H. Rauter GmbH & Co. Vitablocs TriLuxe for CEREC. Brochure. Date of Issue: Mar. 2005.*
(Continued)

*Primary Examiner* — David Sample
*Assistant Examiner* — Nicholas W Jordan
(74) *Attorney, Agent, or Firm* — Christie, Parker & Hale LLP (57) ABSTRACT

A dental blank of the present invention has at least an inner zone (or layer) of a first color and an outer zone (or layer) of a second color wherein the inner and outer zones are concentric The inner zone can be surrounded in its entirety by the outer zone such that only the outer zone is visible on all surfaces of the blank and the inner zone is not visible on any surface of the blank Alternatively, the inner zone and the outer zone can extend to a same single surface of the blank, such that only the outer zone covers all remaining surfaces The dental blank may also have an intermediate zone between the inner and outer zones, wherein the intermediate zone is surrounded in its entirety by the outer zone and/or the intermediate zone surrounds the inner zone in its entirety.

6 Claims, 11 Drawing Sheets

(56) References Cited

U.S. PATENT DOCUMENTS

| | | | |
|---|---|---|---|
| 4,828,117 A * | 5/1989 | Panzera et al. | 206/63.5 |
| 5,151,044 A * | 9/1992 | Rotsaert | 433/229 |
| 5,308,243 A * | 5/1994 | Emmons | 433/203.1 |
| 5,591,030 A * | 1/1997 | Thiel et al. | 433/212.1 |
| 6,488,503 B1 * | 12/2002 | Lichkus et al. | 433/202.1 |
| 6,660,400 B1 | 12/2003 | Hintersehr | |
| 2002/0076530 A1 | 6/2002 | MacDougald et al. | |
| 2003/0031984 A1 | 2/2003 | Rusin et al. | |
| 2003/0207235 A1 | 11/2003 | der Zel | |

OTHER PUBLICATIONS

International Search Report dated May 16, 2008 for International Application PCT/US2007/089157, 4 pages.

Supplemental European Search Report dated May 11, 2012 for European Application No. EP 07 86 6126, 6 Sheets.

Communication from European Patent Office for EP Application No. 07 866 126.1, dated Jan. 18, 2013, 6 pages.

Communication from European Patent Office for EP Application No. 07 866 126.1, dated Aug. 27, 2013, 8 pages.

Communication from European Patent Office for EP Application No. 07 866 126.1, dated Feb. 28, 2014, 5 pages.

Communication from European Patent Office Board of Appeal for EP Application No. 07 866 126.1 (Appeal No. T0305/14-3.2.08), dated Apr. 28, 2014, 12 pages.

European Patent Office Communication dated Apr. 28, 2014 for EP Patent Application No. 07866126.1, 12 pgs.

* cited by examiner

MULTICOLOR DENTAL BLANKS AND RELATED METHODS

CROSS-REFERENCE TO RELATED APPLICATIONS

This application is a 371 of PCT/US07/89157, filed Dec. 28, 2007, which claims priority to and the benefit of U.S. Provisional Application No. 60/878,041, filed Dec. 28, 2006, the content of which is incorporated herein by reference.

FIELD OF THE INVENTION

The invention relates to methods and materials for machinable multicolor dental blanks to fabricate polychromatic, color-graded dental devices which replicate the color gradation of natural teeth.

BACKGROUND OF THE INVENTION

Presently, dental blanks are composed of a single color, or of multiple colors layered on top of each other. The monochromatic blocks may not match the natural color gradation found in natural teeth. Furthermore, shades of these colored blocks are limited in number, and may not even match an overall base shade of a tooth.

One known type of block does have three layers of color. However, these layers extend fully to surfaces of the block, and result in restorations with sharp gradations in color, as opposed to natural teeth which have gradual changes in color. Furthermore, natural teeth have color generated internally by overlapping colors from the enamel and dentin of the tooth.

Conventional methods of fabricating dental blocks involve pressing powders into a mold or using an extrusion from which blocks are then fired to full density. These are time and labor intensive processes and do not easily allow for placement of multiple colors as desirable for dental blocks with improved color matching.

Accordingly, it would be desirable to provide a blank with color zones which correspond to colors found in natural teeth. Moreover, it would be desirable to provide a blank from which restorations with varying ratios of color thicknesses can be produced. It would also be desirable to provide a method of fabrication of dental blocks that readily allows for placement and incorporation of multiple colors.

SUMMARY OF THE INVENTION

The proposed blank has concentric zones of color which correspond to colors found in natural teeth. A restoration may be positioned in the blank to produce a milled restoration with layered overlapping colors. The resulting milled restoration more closely resembles the layering found in natural teeth. Furthermore, the restoration may be positioned in the blank to produce varying ratios of color thickness which allows for production of multiple shades from a single blank. Blocks currently on the market are a single shade, or are limited in the number of shades available. The proposed blank would allow for more shades to be produced, and thus improve the likelihood of a match to the patient's natural dentition.

In one embodiment, a dental blank of the present invention has at least an inner zone of a first color and an outer zone of a second color, wherein the inner and outer zones are concentric. The inner zone can be surrounded in its entirety by the outer zone such that only the outer zone is visible on all surfaces of the blank and the inner zone is not visible on any surface of the blank. Alternatively, the inner zone and the outer zone can extend to a same single surface of the blank, such that only the outer zone covers all remaining surfaces.

In a more detailed embodiment, the inner zone has a first chroma and the outer zone has a second chroma, wherein the first chroma is greater than the second chroma, or the color of the inner zone is darker than the color of the second zone.

In another embodiment, the dental blank has an intermediate zone between the inner and outer zones. The intermediate zone can be surrounded in its entirety by the outer zone and/or the intermediate zone surrounds the inner zone in its entirety, or the intermediate zone can extend to the same single surface of the blank to which the inner and outer zones extend.

The dental blank may have a generally rectangular configuration or a generally cylindrical configuration. The zones may have a generally rectangular configuration or a generally cylindrical configuration, wherein the configuration of the zones is independent of the configuration of the blank. Some or all of the zones may also have the same thickness or different thicknesses.

In another detailed embodiment, the invention comprises a blank of concentric polychromatic (typically three or more colors) material. The blank is composed of porcelain, ceramic, glass, glass ceramic, composite resin, acrylic, or other machinable or heat-pressable material. A holder, if needed, of metal, plastic, or a combination of these materials may be glued directly on the blank, or the blank may be molded directly on the holder for placement in a milling device.

The present invention also includes fabrication of dental blanks through solid free form processes, such as robocasting, laser sintering and 3D printing that readily allow for placement of multiple colors in a single dental blank. A method of manufacturing a dental blank includes solid free form fabricating a dental blank having at least a first and a second concentric zones, wherein the first concentric zone has one color and the second concentric zone has another color. The solid free form fabrication can be robocasting, three dimensionally printing or laser sintering. In a more detailed embodiment, the solid free form fabricating a dental blank includes providing a depositing device adapted to deposit a material of a first color and a material of a second color, providing a platform, wherein the depositing device and the platform move in a predetermined pattern relative to each other, and controlling the depositing device to switching between depositing the material of the first color and depositing the material of the second color. The predetermined pattern can be a spiral, a raster, or variations or combinations thereof.

The methods and materials for producing milled dental devices of the present invention can overcome shortcomings of prior-art devices. The methods and materials for producing dental blanks of the present invention can be applied to fabricate polychromatic, color-graded dental devices which replicate the color gradation of natural teeth. The methods and materials for producing dental blanks of the present invention can also allow for the production of a variety of shades from a single block of material by varying the ratio of milled outer layers to internal layers.

DETAILED DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

A blank in accordance with the present invention is composed of porcelain, ceramic, glass, glass ceramic, acrylic, composite resin, a combination of some of these materials, or other materials with concentric colors representing natural tooth colors. Colorants may be inorganic or organic. A suitable porcelain may be composed of a variety of materials with a glass matrix such as feldspathic glasses, silica, aluminosilicates, and crystalline materials such as leucite, fluorapatite, fluoromica, with other metallic oxides as colorants or matrix/crystal components. Ceramic materials may include metallic oxides such as alumina, zirconia, spinel or other monocrystalline or polycrystalline materials. As understood by one of ordinary skill in the art, ceramics and porcelains may contain inorganic colorants to achieve the proper color gradation to match natural teeth. Moreover, acrylic and composite resins may be composed of methacrylates such as methyl methacrylate or urethane dimethacrylate, BIS-GMA, epoxies, polyacrylamide, with or without glass, ceramic, or fibers commonly used as fillers for direct or indirect resin-based restorative materials.

As illustrated in FIGS. 1-14, a blank (or block, used interchangeably herein) B of the present invention may be in the form of a cylinder of various diameters and lengths, or a rectangle of various dimensions, e.g., widths, lengths and heights. In any of these forms, the blank has at least two opposing surfaces S1 and S2. In the case of a rectangular blank BR (inclusive of a square blank) as illustrated in FIGS. 1-4, there are the opposing surfaces S1 and S2 with four additional surfaces S3-S6 extending therebetween. In the case of a cylindrical blank BC as illustrated in FIGS. 5-8, there are the opposing surfaces S1 and S2 and a tubular surface ST extending therebetween.

In accordance with a feature of the present invention, the blank B whether it is cylindrical or rectangular (or any other shape) is configured with a plurality of concentric zones (or layers) of colors $Z_1, Z_2, \ldots Z_n$, with the plurality n ranging between about 2 to 5, and more preferably about 3. The zones may be of varying sizes/volumes/thicknesses, and varying degrees of chroma, hue and value. Typically two or three zones of color extend from darker to lighter, and/or higher chroma to lower chroma, as one proceeds from an innermost or internal zone $Z_1$, to middle or intermediate zone(s) $Z_i$ and to an outermost or external zone $Z_n$.

In one embodiment of the blank, all of the concentric zones extend to one of the surfaces S1 or S2, such that all of the concentric zones are visible on that one surface only. In the embodiment of FIGS. 5-8, all of the concentric zones Z1-Z3 of the cylindrical blank BC are visible on surface S1, whereas only the outermost zone Z3 is visible on the remaining surfaces S2 and ST. In the embodiment of FIGS. 1-4, all of the concentric zones Z1-Z3 of the rectangular blank BR are visible on surface S1, whereas only the outermost zone Z3 is visible on the remaining surfaces S2, and S3-S6.

It is understood by one of ordinary skill in the art that with either the blank BC or BR, each of the surfaces except for the surface on which the concentric zones are visible (namely S1 in the illustrated embodiments) presents a surface underneath which the different zones Z1-Zn are layered to advantageously simulate the layering structure found in natural teeth. The concentric zones and colors are contained within the block, with outwardly decreasing chroma, and with possible differences in shade and opacity. The change in chroma progresses from an internal layer Z1, through an intermediate layer Zi, to an external layer Zn. In accordance with a feature of the present invention, a resulting color and chroma that is visible on the surfaces on which only the outermost zone Zn is visible (namely, all surfaces except for the surface S1) is composed of a combination of the colors and chromas of all the zones layered below the surfaces of the blank.

In another embodiment, only the outer zone Zn extends to the surfaces of the blank. As illustrated in FIGS. 10-13, the innermost zone Z1 is surrounded entirely by the intermediate zone Z2, which in turn is surrounded entirely by the outermost zone Z3. Accordingly, only the outermost zone Z3 is visible on all surfaces of the blank. In accordance with a feature of the present invention, the color and chroma visible on all of the surfaces of the blank is a combination of all the colors and chromas of all the zones that are layered under the surfaces of the blank.

In the illustrated embodiments of FIGS. 1-8 and 10-13, the zones have a cross section or overall shape that mirrors the cross section or overall shape of their respective blank. That is, the zones of the rectangular blank BR have a generally rectangular shape and the zones of the cylindrical blank BC have a generally cylindrical shape. Conceivably, the zones may not mirror the shape of their respective blank, and a cylindrical blank can have rectangular zones, and a rectangular blank can have cylindrical zones, or a blank can even have a mix of rectangular or cylindrical zones as appropriate or desired.

Figure 9:
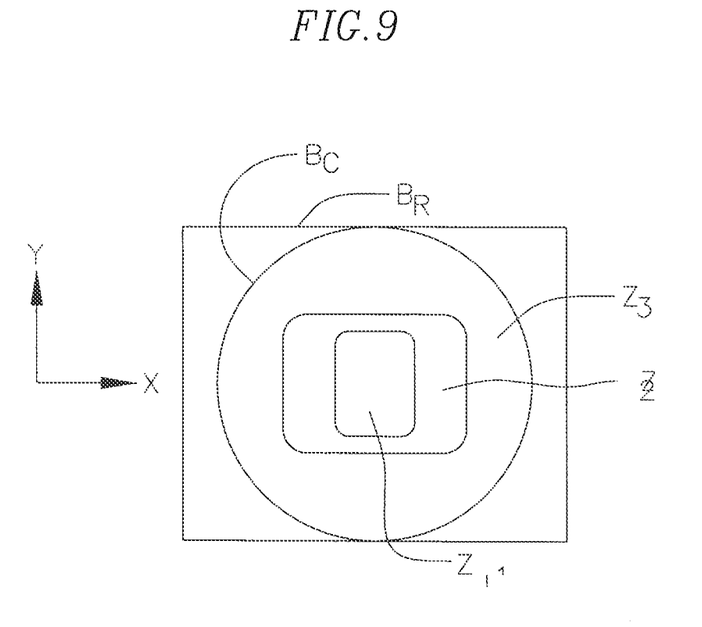
FIG. 9 is a side view of another embodiment of a dental blank showing concentric zones with different configurations and/or thicknesses.
Figure 10:
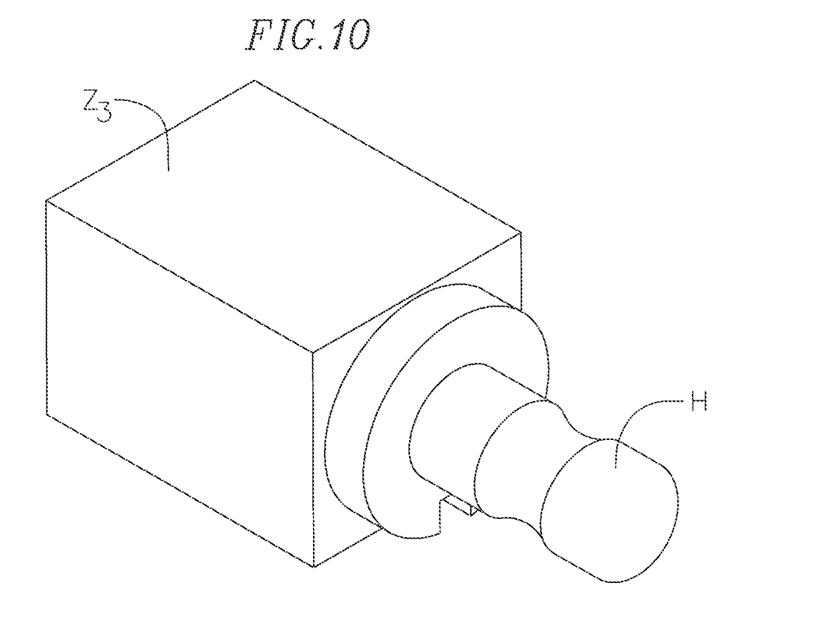
FIG. 10 is a perspective view of another embodiment of a dental blank of the present invention, whose internal concentric zones do not extend any surface of the dental blank.
Figure 10A:
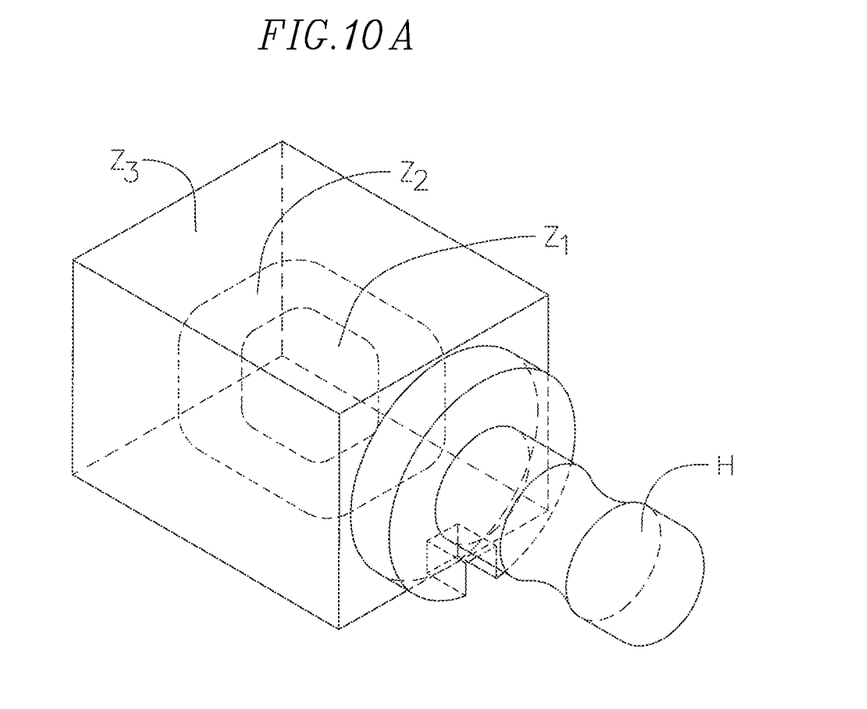
FIG. 10A is a perspective view of the dental blank of FIG. 10 showing concentric zones.
Figure 11:
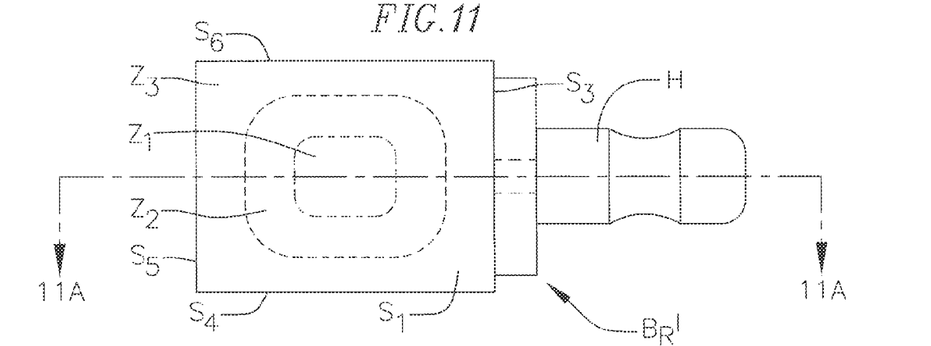
FIG. 11 is a top view of the dental block of FIG. 10.
Figure 11A:
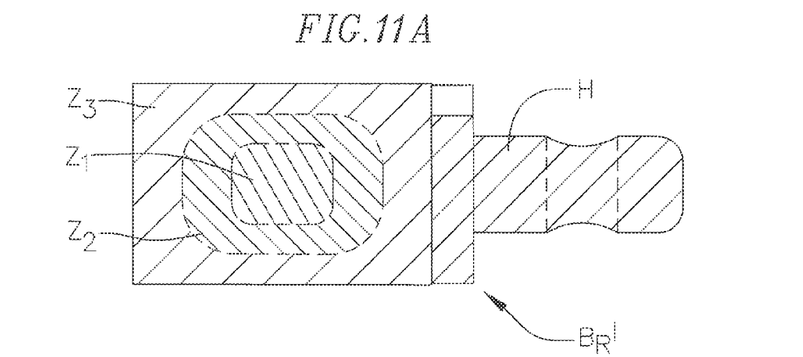
FIG. 11A is a cross-sectional view of the dental block of FIG. 11 taken along line A-A.
Figure 12:
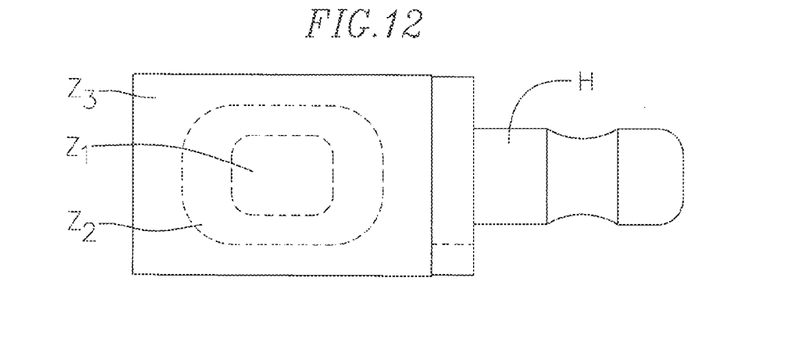
FIG. 12 is a side elevational view of the dental block of FIG. 10.
Figure 13:
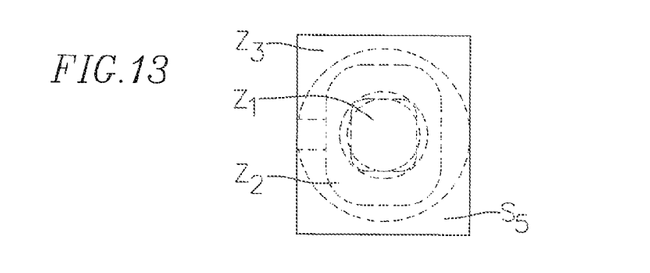
FIG. 13 is an end view of the dental block of FIG. 10.

Moreover, the zones within a blank can have the same or different thicknesses, and the thickness of any one zone can also be varied in different dimensions, for example, in the (X,Y,Z) Cartesian coordinates, or (R, Z) polar coordinates. In the illustrated embodiments, the zones Z2 and Z3 of the block BR are generally thicker than the zone Z1, and the zone Z2 of Block BC is thinner than both zones Z1 and Z3. As illustrated in FIG. 9, the block whether it is a rectangular block BR or a cylindrical block BC, a zone (such as zone Z2) can have a greater thickness in one dimension (e.g., X axis) and a lesser thickness in another dimension (e.g., Y axis).

Figure 16:
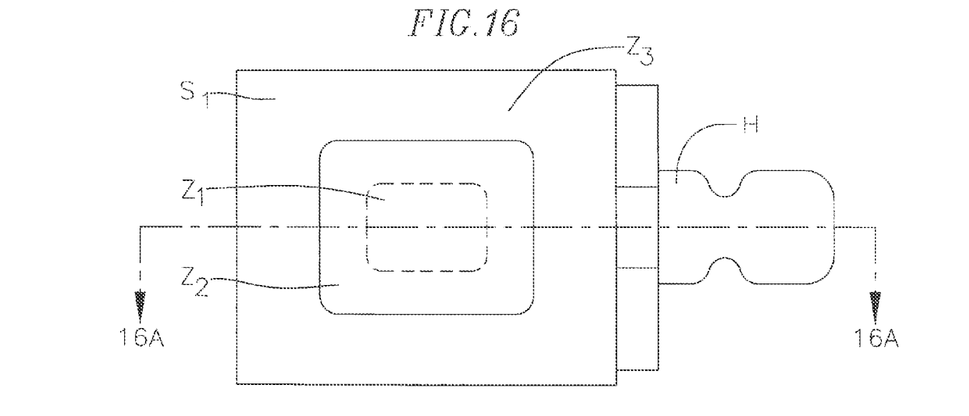
FIG. 16 is a top view of yet another embodiment of a dental block of the present invention.
Figure 16A:
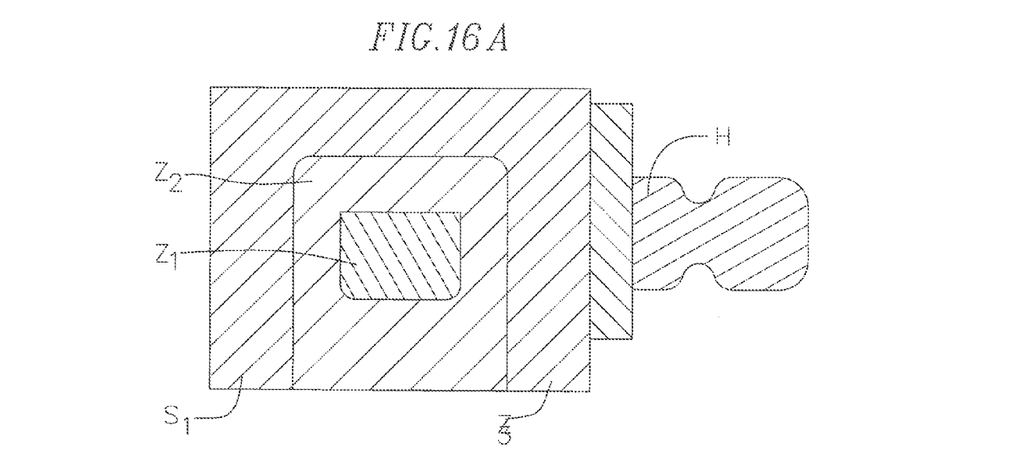
FIG. 16A is a cross sectional view of the dental block of FIG. 16, taken along line A-A.

Furthermore, the zones within a blank may be varied in whether they extend to a surface of the blank. As illustrated in FIGS. 16 and 16A, the zone Z1 may be surrounded entirely by zone Z2 and not extend to any surface of the blank, but the zone Z2 may extend to the surface S1. Indeed, any variation in the configuration or the thickness of the zones is contemplated within the present invention, as desired or appropriate. However, in accordance with a feature of the present invention, the zones remain generally concentric.

The blank may be made partially or completely opaque, and may be colored to match natural tooth colors or other colors. Additional materials may be added to the milled devices to further alter color or shape. The blank may be positioned in a milling device to alter a ratio of milled external colors to internal colors to produce multiple tooth shades from a single blank.

The blank may be used directly as a final or provisional restoration. The blank may be milled to provide a substructure for other materials layered on the milled blank to produce a final or provisional restoration.

In one embodiment, a porcelain blank is placed in a spindle of a milling device. The blank is milled to form a full-contour dental restoration, using computer design and milling. A proper blank is selected for the tooth color being matched, and is placed in the milling system. The blank is milled to provide an inner layer(s) of darker, more chromatic material, with an outer layer(s) of lighter, less chromatic material. This replicates the gradation in color found in the tooth being restored, and in the adjacent natural teeth. In the illustrated embodiments, the innermost layer Z1 provides the darker, more chromatic material and the outermost layer Zn provides the lighter, less chromatic material.

Figure 1:
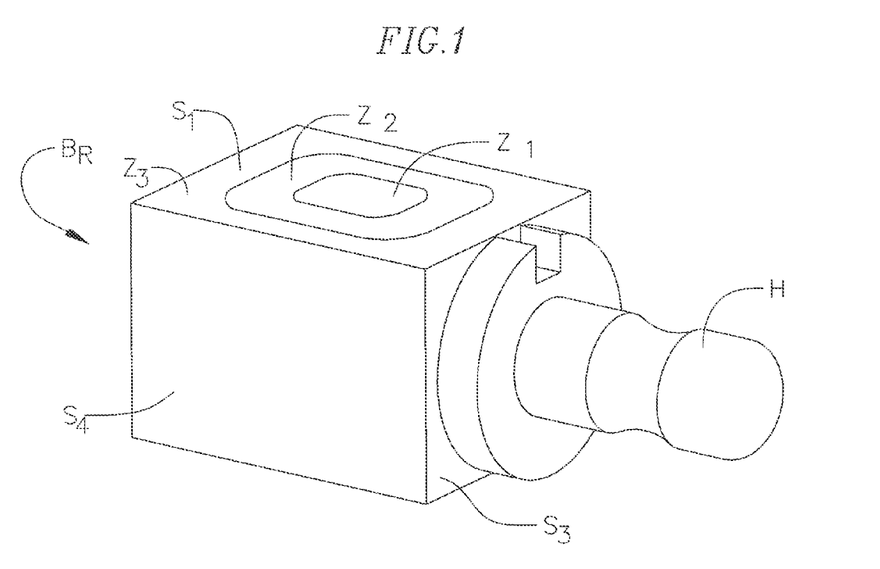
FIG. 1. is a perspective view of one embodiment of a dental blank of the present invention.
Figure 1A:
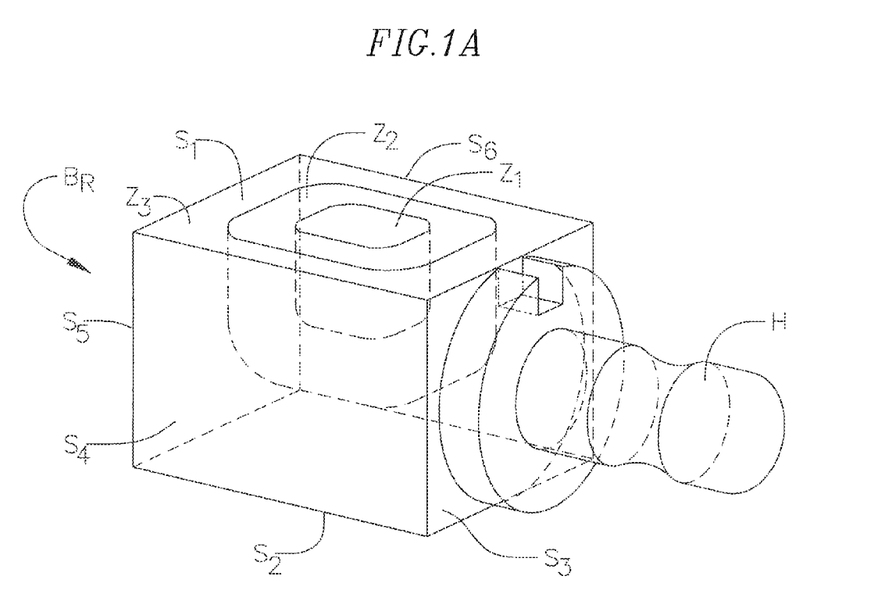
FIG. 1A is a perspective view of the dental blank of FIG. 1 showing concentric zones.
Figure 2:
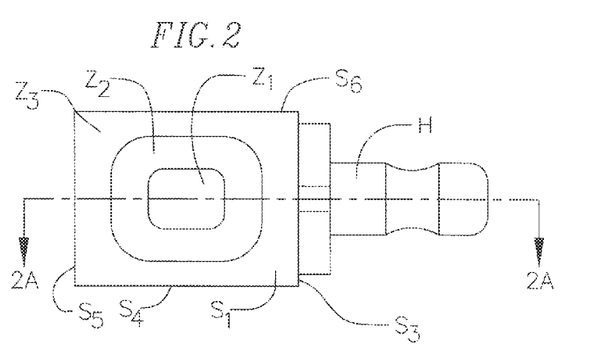
FIG. 2 is a top view of the dental block of FIG. 1.
Figure 2A:
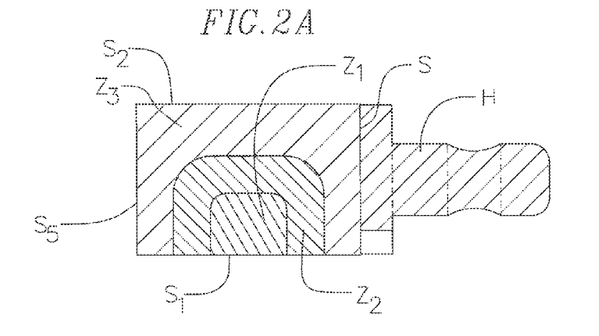
FIG. 2A is a cross-sectional view of the dental block of FIG. 2 taken along line A-A.
Figure 3:
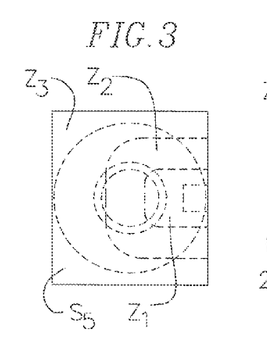
FIG. 3 is an end view of the dental block of FIG. 1.
Figure 4:
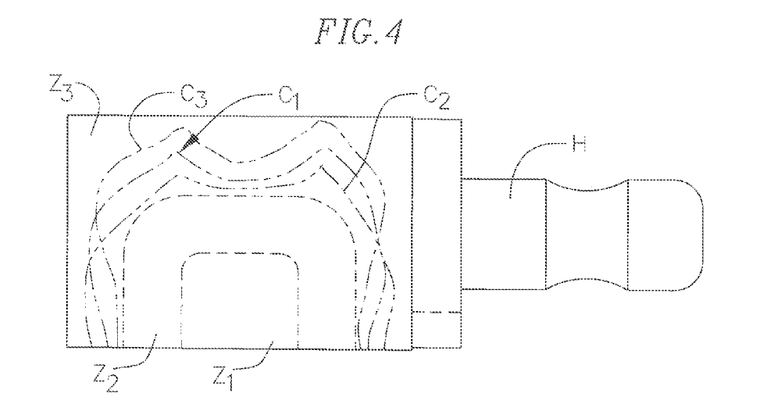
FIG. 4 is a side elevational view of the dental block of FIG. 1, with restoration contour lines C1, C2 and C3.
Figure 5:
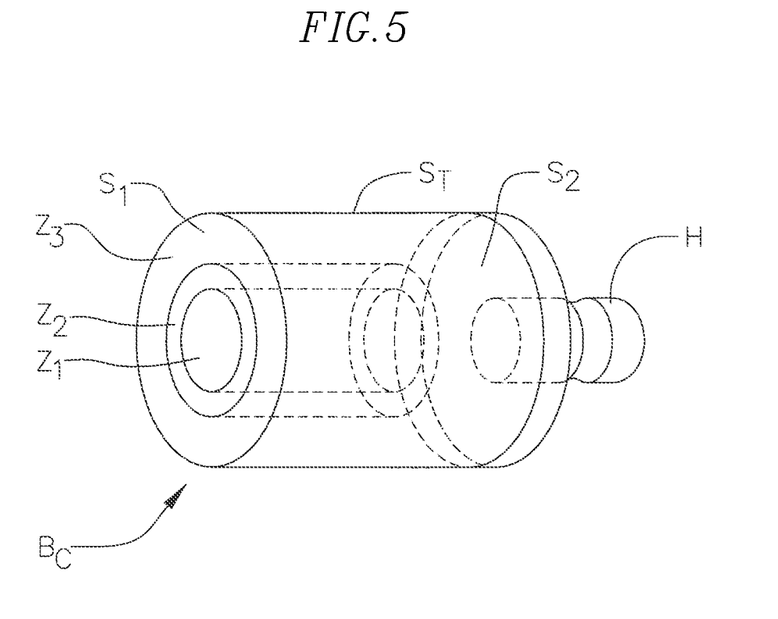
FIG. 5 is perspective view of another embodiment of a dental blank of the present invention.
Figure 6:
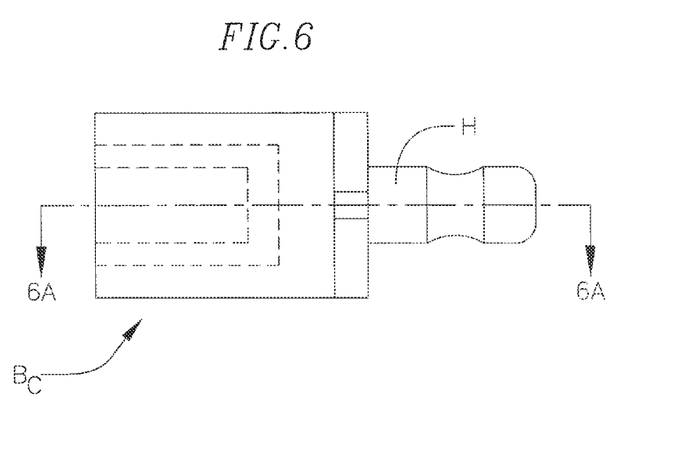
FIG. 6 is a top elevational view of the dental blank of FIG. 5.
Figure 6A:
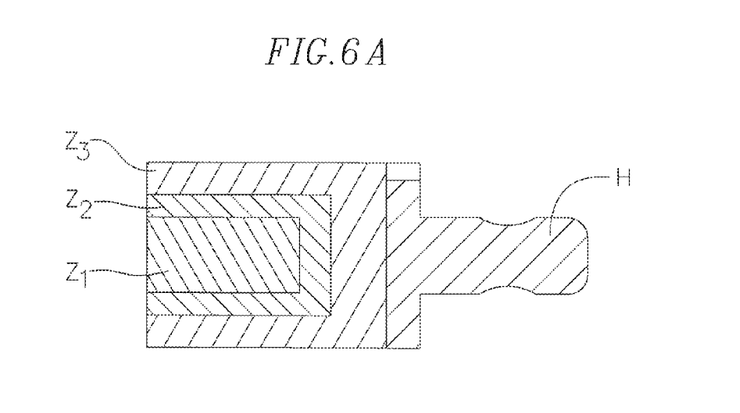
FIG. 6A is a cross-sectional view of the dental blank of FIG. 6, taken along line A-A.
Figure 7:
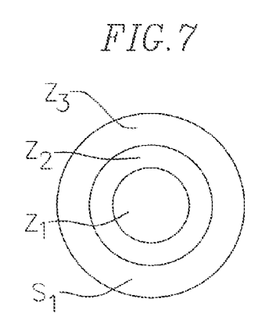
FIG. 7 is an end view of the dental blank of FIG. 6.
Figure 8:
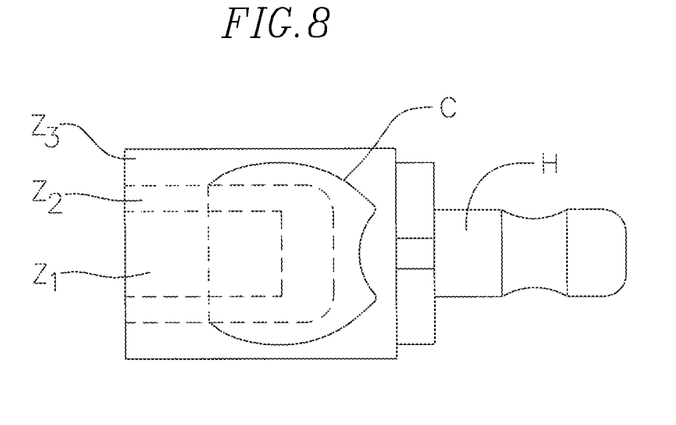
FIG. 8 is a top view of the dental blank of FIG. 6, showing a restoration contour line C.

A holder H comprised of metal, plastic or a combination thereof, may be attached to the blank for placement in the milling device. The holder may be glued to the blank, or the blank may be directly processed on the holder. The holder H may be fixed to the block in order to facilitate positioning in the milling device. This may or may not be necessary, and the holder is not limited to the exact configuration as illustrated. Referring to FIG. 4, the block may be milled to produce a full-contour restoration, such as a crown C. The layers Z1, Z2 and Z3 represent the natural layering of color seen in a tooth. An outline of the crown C1 is shown in FIG. 4. Notably, the surface S1 on which all zones of the blank are visible coincides with a bottom of the crown C1, that is, a surface for which there is minimal need for matching color with natural teeth. Correspondingly, all other surfaces of the crown C1 lie in an area underneath which is a layering of the various zones of the blank. And, by adjusting the outline of the crown C1 in FIG. 4, the thickness of the outermost zone Z3 at any region can be varied so as to vary the resulting color/chroma in that region. For example, where the outline is lowered to C2, the crown has a thinner layer of Z3 on its biting or occlusal surface. And, where the outline is raised to C3, the crown has a thicker layer Z3 on its occlusal surface. Similarly, a shift to the left or right in FIG. 4, can result in the crown having a thinner or thicker layer of Z3 on its facial or lingual surface. Since a difference in the thickness of the layer of Z3 can affect color/chroma, the crown following outline C2 has a different color/chroma from the crowns following outlines C1 and C3. However, all crowns C1, C2 and C3 have the benefit of a more natural looking color/chroma resulting from the layering effects of zones Z1, Z2 and Z3.

Figure 14:
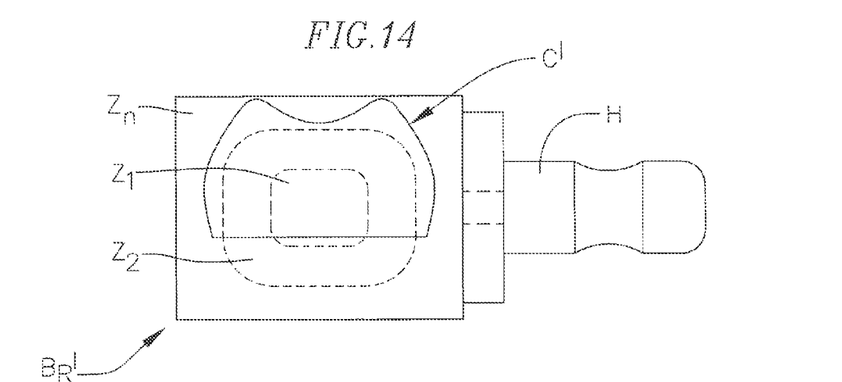
FIG. 14 is a top view of the dental block of FIG. 10, showing a restoration contour line C'.

FIGS. 10-13 illustrate another embodiment of a multicolor rectangular bank BR' (although it is understood that the following description applies to a cylindrical blank). In this embodiment, the inner zones or layers are surrounded in their entirety by the outer zones or layers so that only the outermost zone Zn (in this instance Z3) is visible on the surface S1. Also in this embodiment, the chroma decreases from an internal layer Z1, to an intermediate layer Z2, and then is lowest at an outer layer Z3. Furthermore, as with the previous embodiments, the opacity and color may also change. FIG. 14 illustrates a full-contour crown fabricated using this block embodiment block. An outline C' of the crown is depicted. Again, it is understood that by adjusting the placement of the outline C', the thickness of the layer of Z3 can be increased or decreased in all three dimensions of X, Y and Z.

Figure 15:
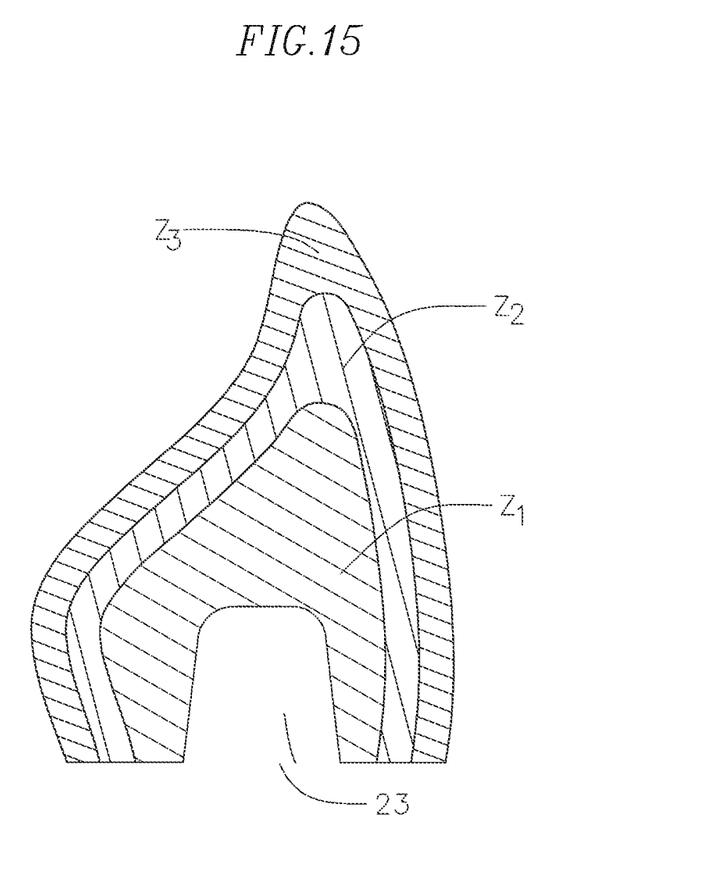
FIG. 15 is a cross sectional view of an embodiment of a milled dental block of the present invention.

FIG. 15 illustrates one embodiment of a milled full-contour crown in which three layers of increasing chroma have been used. As illustrated, each zone Z1-Z3 has a similar configuration resembling that of the crown or the resulting dental device/prothesis. A lower-central area 23 contains no material, and fits on a mating portion of a prepared tooth. Chroma outwardly decreases from an inner layer or zone Z1 (highest chroma) through a middle layer or zone Z2, to an outer layer or zone Z3 (lowest chroma). Shade and opacity may also be varied across these layers. Furthermore, varying the thickness ratio of the three layers) may allow fabrication of a variety of tooth shades from a single block.

Regardless of the specific embodiment of a blank, a method of milling a dental prosthesis from the blank can include using a blank with concentric zones of different colors, including an outermost zone, and positioning a form of the dental prosthesis on the blank wherein an occlusal surface of the prosthesis is contained in the outermost zone, so that the occlusal surface provides a resulting color/chroma that results from the combination of colors/chromas of the underlying zones. And, by adjusting the positioning of the form on the blank, the resulting color/chroma can be adjusted.

Advantageously, position of the block may be altered in the milling system to allow for improved color replication and production of multiple tooth shades from a single block.

Alternatively, the blank may be milled to provide a substructure upon which additional colored layers may be applied to produce the final dental restoration.

Alternatively, the above procedures may be followed to produce a provisional restoration.

Alternatively, the blank may be milled to produce a superstructure, which is then joined to a substructure by gluing or firing, using an intermediary glass, porcelain or ceramic material.

Alternatively, the blank may be milled to produce a denture tooth.

Alternatively, the blank may be heated until flowable, and pressed or molded into a tooth pattern to fabricate the dental restoration.

The multicolor layered blank may be fabricated by sequential pressing, injection molding, or three-dimensional rapid manufacturing techniques. These include selective laser sintering, three-dimensional printing, or Robocasting/Direct slurry deposition, or deposition of a suspension of the component materials.

Selective Laser Sintering is an additive rapid manufacturing technique that uses a high power laser (for example, a carbon dioxide laser) to fuse small particles of plastic, metal, or ceramic powders into a mass representing a desired 3-dimensional object. The laser selectively fuses powdered material by scanning cross-sections generated from a 3-D digital description of the part (e.g. from a CAD file or scan data) on the surface of a powder bed. After each cross-section is scanned, the powder bed is lowered by one layer thickness, a new layer of material is applied on top, and the process is repeated until the part is completed.

Three-dimensional printing is a method of converting a virtual 3D model into a physical object. 3D printing is a category of rapid prototyping technology. 3D printers typically work by printing successive layers on top of the previous to build up a three dimensional object.

Robocasting is a method of fabricating ceramics that requires no molds or machining, by generally relying on robotics for computer-controlled deposition of ceramic slurries—mixtures of ceramic powder, water, and trace amounts of chemical modifiers—through a syringe. The material, which flows like a milkshake even though the water content is only about 15 percent, is deposited in thin sequential layers onto a heated base. The product manufactured is fabricated layer by layer by a robot that squeezes a slurry out of the syringe, following a pattern prescribed by computer software. A suitable robocasting method is described in U.S. Pat. Nos. 6,027,326, and 6,401,795, the entire disclosures of which are hereby incorporated by reference.

Figure 17:
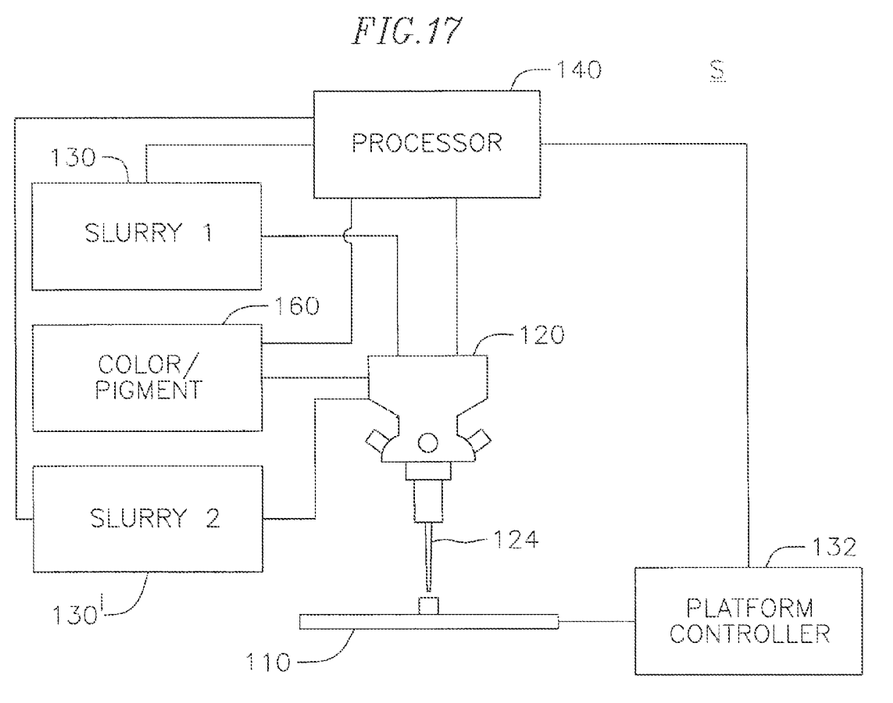
FIG. 17 shows a schematic representation on an embodiment of a system in accordance with the present invention.

The foregoing techniques and other types of solid free form fabrication allow for placement of multiple colors. As illustrated in FIG. 17, an embodiment of a system S for freeforming a dental blank includes a moveable platform 100 and a material depositing device 120 having a nozzle or printer head 124 through which material (e.g., a slurry 1) 130 is controllably deposited. Conventional means are provided for controllably moving depositing device 120 with respect to platform 110 in at least X, Y, and Z directions. As illustrated, platform 110 may be an X-Y table which is moveable in the X-Y plane by a platform controller 132, and device 120 may be driven by conventional means, such as a threaded rod in the Z direction. Alternatively, platform 110 may be fixed and device 120 may be affixed to a robotic arm moveable in any direction. In addition, both platform 110 and device 120 may be moveable with respect to one another.

Depositing device 120 may be a syringe or a printer head. The movement of device 120 with respect to platform 110, and actuation of the depositing device 120, is controlled by a programmed processor or computer 140.

To provide the different zones of colors in the blank B, the S system in the illustrated embodiment includes a color or pigment source 160 that is also connected to the processor 140 which controls the amount of color or pigment to be mixed with the slurry 1. Alternatively, the system can include a second material 130' (e.g., slurry 2 with a different color, shade or chroma,) which the processor 140 can select as an alternate source of material for the depositing device 120.

Figure 18:
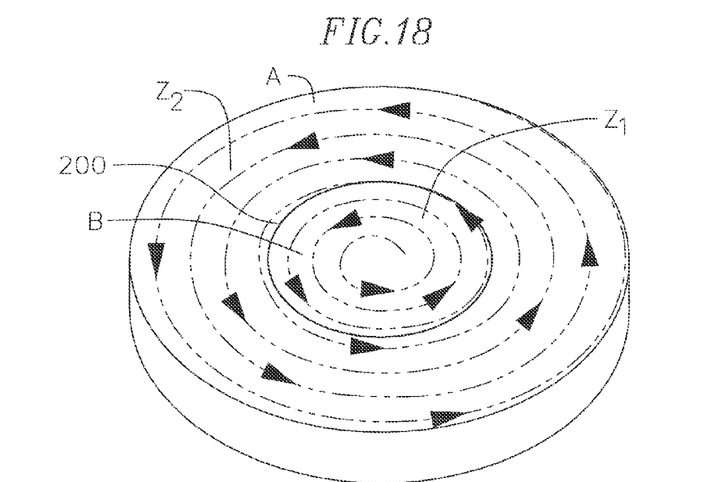
FIG. 18 shows a perspective view of an embodiment of a cylindrical blank as fabricated in accordance with the present invention.
Figure 19:
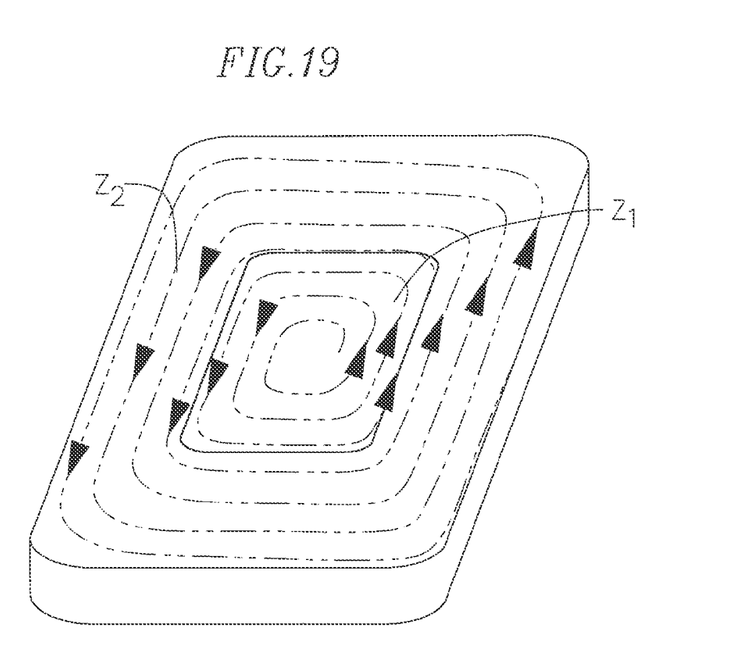
FIG. 19 shows a perspective view of an embodiment of a rectangular blank as fabricated in accordance with the present invention.
Figure 20:
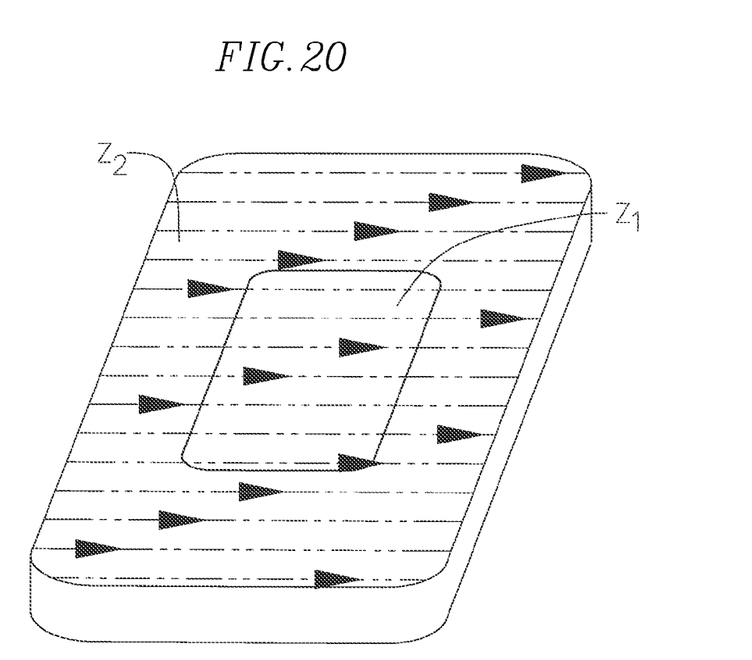
FIG. 20 shows a perspective view of an embodiment of a rectangular blank as fabricated in accordance with the present invention.

With further reference to FIG. 18, in fabricating a cylindrical blank BC, the relative movement between the platform and the depositing device 120 may be a spiral pattern (illustrated in broken lines) that is generally circular. The spiral can be inwardly and/or outwardly, creating layer upon layer of material with each pass over the same location on the blank. In one embodiment, where the blank BC has an inner zone Z1 and an outer zone Z2, the computer 140 starts a deposition process by positioning the depositing device at location A and depositing the slurry II from the material source 130' in an inwardly spiral counterclockwise pattern to begin creating the zone Z2. When the depositing device reaches a boundary or border 200 between the zones Z1 and Z2, the computer 140 changes the amount of color or pigment from the source 160 to be added to the slurry II to begin creating the zone Z1. The deposition process in the zone Z1 continues until the depositing device reaches location B (e.g., a center of the blank), at which stage the computer 140 can reverse the deposition pattern to an outwardly spiral clockwise pattern to add another layer to the zone Z1. When the depositing device again reaches the boundary 200, the computer 140 changes the amount of color back to that used for the zone Z2. Alternatively, when the deposition device reaches the boundary 200, the computer 140 can switch the source of the slurry for the deposition device between materials 130 and 130' for building the zones Z1 and Z2, respectively. It is understood that while the embodiment of FIG. 18 shows the relative movement between the nozzle and the platform as a spiral pattern, the pattern can also be a raster (see FIG. 20), although the frequency in changing the amount of color/pigment input from the color source 160, or in switching between the material sources 130 and 130' would be greater. With reference to FIG. 19, a generally rectangular blank BR can be fabricated with a relative pattern that is generally rectangular. Indeed, the relative pattern can also correspond with or be dependent on the configurations of the zones.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A dental blank comprising at least an inner zone of a first color, an intermediate zone of a second color and an outer zone of a third color, the dental blank having a center, wherein the inner, intermediate and outer zones are concentric relative to each other and to the center of the dental blank, wherein the dental blank has a geometric shape, wherein the inner zone is surrounded in its entirety by the intermediate zone and the intermediate zone is surrounded in its entirety by the outer zone, such that only the outer zone is visible on all surfaces of the blank, and wherein each zone has generally the same geometric shape as the dental blank, and wherein the blank has multiple outer surfaces, each of which has a resulting color that is of a combination of at least the first color of the inner zone, the second color of the intermediate zone and the third color of the outer zone.

2. A dental blank of claim 1, wherein the second color is darker than the third color.

3. A dental blank of claim 1, wherein the first color is darker than the second color.

4. A dental blank of claim 1, wherein the blank has a generally rectangular configuration.

5. A dental blank of claim 1, wherein the blank has a generally cylindrical configuration.

6. A dental blank of claim 1, further comprising a holder.

* * * * *